United States Patent [19]
Lever et al.

[11] Patent Number: 5,196,515
[45] Date of Patent: Mar. 23, 1993

[54] THIOLACTONE BIFUNCTIONAL CHELATING AGENTS FOR DIAGNOSTIC AND THERAPEUTIC PRODUCTS

[75] Inventors: Susan Z. Lever; Kwamena E. Baidoo, both of Baltimore, Md.; Alfred V. Kramer, Upper Providence; Hugh D. Burns, Harleysville, both of Pa.

[73] Assignee: The Johns Hopkins University, Baltimore, Md.

[21] Appl. No.: 755,775

[22] Filed: Sep. 6, 1991

Related U.S. Application Data

[62] Division of Ser. No. 324,859, Mar. 17, 1989, Pat. No. 5,095,111.

[51] Int. Cl.[5] .................. A61K 39/00; A01N 37/18; C07K 3/00; C07K 15/00

[52] U.S. Cl. ................. 530/363; 424/85.8; 424/85.91; 530/382; 530/391.5; 530/388.7; 530/388.85; 530/388.8; 530/389.1; 530/389.3; 540/544;

[58] Field of Search .............. 435/4, 6; 530/387; 424/85.8; 514/2; 540/544; 544/54, 58.2; 548/186

Primary Examiner—David L. Lacey
Assistant Examiner—Gian P. Wang
Attorney, Agent, or Firm—Cushman, Darby & Cushman

[57] ABSTRACT

A bifunctional ligand to compositions produced by reaction of the ligand with compounds containing an amino, thiolate or alcholate group, especially proteins, to chelates produced by complexing ligands with metal such as technetium and rhenium and to diagnostic and therapeutic uses of the complexes.

9 Claims, 4 Drawing Sheets

THIOLACTONE BIFUNCTIONAL CHELATING AGENTS FOR DIAGNOSTIC AND THERAPEUTIC PRODUCTS

This application is a division of application Ser. No. 07/324,859, filed Mar. 17, 1989, now U.S. Pat. No. 5,095,111.

The present invention relates to novel bifunctional ligand to compositions produced by reaction of those ligand with compounds containing an amino, thiolate or alcholate group, especially proteins, to chelates produced by complexing ligands with metals such as technetium and rhenium and to diagnostic and therapeutic uses of said complexes.

BACKGROUND OF THE INVENTION

Site specific radiopharmaceuticals are ones whereby radionuclides attached to biologically active molecules are carried to predetermined locations in the body. Biomolecules which have been utilized to date include receptor specific ligands, metabolic tracers, and proteins such as antibodies and their fragments. As applied to the fields of radioimmunodetection and radioimmunotherapy, the major goals remain the early and sensitive detection of cancer, occult infection and thrombi, as well as more effective therapy.

The bifunctional chelate approach has proved to be of value for incorporation of metals into biologically active molecules such as proteins, see Benisek et al., J. Biol. Chem., Vol. 243, page 4267 (1968), Sundberg et al., Nature, Vol. 250, page 587 (1974), and Sundberg et al., J. Med. Chem., Vol. 17, page 1304 (1974). When an appropriate ligand is attached via a covalent bond to the protein, specific coordination of the metal to the ligand preferentially occurs, yielding a labeled product which generally exhibits enhanced in vivo stability, see Meares et al., Accts. Chem. Res., Vol. 17, page 202 (1984), Hnatowich et al., Int. J. Appl. Radiat. Isot., Vol. 33, page 327 (1982), and Paik et al., Int. J. Nucl. Med. Biol., Vol. 12, page 3 (1987). The success of this method for a particular purpose relies upon two principal factors. First, the bifunctional chelate must covalently bind to the protein under conditions which do not adversely affect the protein. In addition, it must possess a high affinity for the metal, so that the metal binds specifically to the chelate. In recent years, there has been much interest in the use of the bifunctional chelate approach for the radiolabeling of proteins with technetium-99m in the field of diagnostic Nuclear Medicine, see Fritzberg, A. R., Nucl. -Med., Vol. 26, page 7 (1987).

This technology has enabled detection of primary and metastatic tumors, using antibodies from monoclonal or polyclonal sources, both in animal models and in man. In the therapeutic arena, partial and total remission of several cancers including hepatomas, Hodgkins' disease and B cell lymphoma have been reported even for patients where other therapeutic regimens have failed. Although progress has been made in this multifaceted research area, many significant problems remain. Optimum imaging protocols, appropriate dosimetry and background reduction techniques are just a few aspects which are the subject of continued research efforts. A major determinant for successful radioimmunodetection and radioimmunotherapy is the development of efficient, reproducible labeling methodologies yielding products in which the radionuclide is attached to the protein in a stable manner while maintaining protein viability.

For diagnostic imaging, technetium-99m (Tc-99m) possesses the best characteristics among currently available radionuclides. Its high photon yield per disintegration ensures good counting statistics with most protocols. The mono-energetic gamma photons are ideally suited for planar and single photon emission computed tomography (SPECT) instrumentation. These 140 KeV photons are soft enough to be adequately collimated while they are hard enough to penetrate overlying tissue for external detection with high sensitivity. The short half life ($T_{\frac{1}{2}}$, 6 hours) and lack of particulate emissions generally result in low absorbed radiation dose. In addition, Tc-99m is inexpensive, approximately $1/mCi, and is widely available in generator form. Because of these properties, there is considerable interest in developing radiopharmaceuticals containing this radionuclide. Indeed, recent studies have demonstrated the applicability of Tc-99m to radioimmunodetection despite its short half life.

Of the radionuclides used for therapeutic applications, Re-186 ($\beta$-$_{max}$ 1070 KeV; gamma 137 KeV, 9%; $T_{\frac{1}{2}}$ 90 hours) and Y-90 ($\beta$-$_{max}$ 2290 KeV; gamma none; $T_{\frac{1}{2}}$ 64 hours), have been judged the best. These radionuclides possess strong $\beta$- emissions capable of delivering high doses to tissues. An important advantage of Re-186 over other therapeutic radionuclides is the associated emission at practically the same energy as Tc-99m; thus, it is possible to follow its biodistribution with the same external scintigraphic equipment used for Tc-99m. Also, Re and Tc are congeners in the periodic table of elements and share certain similar chemical properties. This provides a rationale for designing therapeutic Re analogs of existing diagnostic Tc agents.

Early methods for labeling proteins with Tc-99m relied on the native protein to offer the stabilization needed for reduced Tc and are fraught with problems of weak non-specific labeling, colloidal contamination, protein denaturation and loss of label in vivo. Due to the advantages that the bifunctional chelate approach can provide, it is under investigation for the labeling of proteins with metallic radionuclides such as Tc-99m and Re-186. However, the bifunctional chelating agents (BCAs) used with other radionuclides have met with only limited success for Tc-99m and Re-186. For example, several attempts have been made to use diethylenetriaminepentaacetate (DTPA) coupled proteins to accept reduced Tc-99m. The major problem with proteins labeled in this manner is the lack of sufficient in vitro and in vivo stability. In our experience with Tc-99m labeled DTPA coupled to human immunoglobulin G (IgG), 40% of the radiolabel was lost from the protein within 3 hours in vitro. Furthermore, proteins compete with DTPA for reduced Tc which leads to non-specific binding of Tc to low affinity sites on the protein (Lanteigne and Hantowich, Int. J. Appl. Radiat. Isot., Vol. 35, pages 617-621 (1984)). In order to avoid the incorporation of Tc to weak binding sites, the labeling step can be performed in the presence of excess free DTPA ligand. However, this leads to low yields of Tc-bound protein and does not solve the problem of in vivo transchelation to other proteins. Similarly, an attempt to label DTPA coupled proteins with Re-186 also resulted in very low yields.

Some of the ligands which form complexes with technetium-99m are described in U.S. Pat. No. 4,638,051 and patents and publications cited therein.

It was desirable that a BCA be designed to meet a number of criteria. First, it must form a kinetically stable 1:1 complex with Tc-99m. Then, it must exhibit favorable exchange kinetics with a pre-formed labile Tc complex under mild labeling conditions. The BCA, as well as the reaction conditions used to couple it to the protein, or other sensitive biomolecules must be compatible with sensitive biomolecules such that direct conjugation of the ligand to protein via a covalent bond occurs under mild conditions.

The requirement for 1:1 stoichiometry between the ligand and Tc will ensure that no aggregation of the coupled protein would occur as a result of the complexation process. The strong chelating ligand should be able to extract reduced Tc-99m efficiently from the pre-formed Tc-99m complex as well as from any labile sites on protein. The rate of transchelation should be fast relative to the half-life of Tc-99m. Compatibility with the protein is desirable to ensure that the ligand itself does not cause denaturation of the protein. The strong BCA should directly couple to the protein without additional activation.

European Patent Application 0 188 256 discloses metal chelating compounds which are dithio-, diamino- or diamidocarboxylic acids or derivatives thereof and appears to have tried to claim a diaminodithiol (DADT) chelating ligand system. The compounds are intended for complexing with radionuclides.

U.S. Pat. No. 4,434,151 discloses the use of thiolactone as a coupling agent, but the agent is not internal in nature.

SUMMARY OF THE INVENTION

The present invention is concerned with novel bifunctional ligands for the facile and efficient incorporation of technetium, rhenium, indium or yttrium into biomolecules under mild conditions. The chelating agent consists of an internal thiolactone built on the backbone of the strong chelating aminethiol system. The thiolactone moiety provides a reactive functionality to allow attachment of the agent to proteins via stable amide bond formation with free amino groups on proteins. Reaction of the thiolactone in this way releases a previously masked thiol group to complete the coordinate core of the chelating system. The overall effect is the introduction of a strong chelating ligand through a covalent bond to the protein. Since the reactive thiolactone functionality is internal, the BCA requires no activation prior to coupling. No byproducts of the reaction are released into solution which might affect protein viability. Further, the full coordinating potential of both amine groups is maintained for facile complex formation.

These ligands have the following general structure:

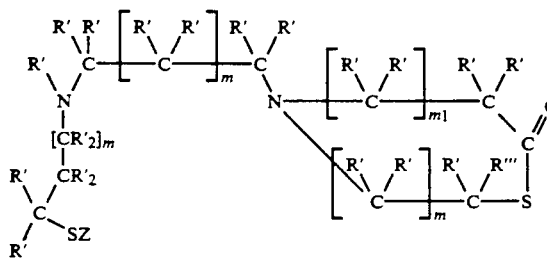

where Z = H, or labile thiol- protecting group

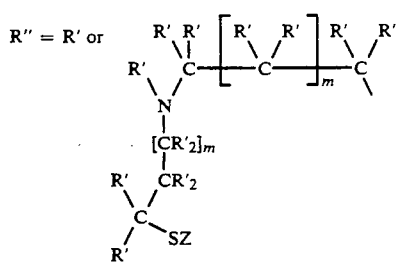

Wherein each R' is independently a hydrogen atom or an alkyl group, preferably a lower alkyl group, or substituted lower alkyl wherein the substituent can be any ester, R" and R"' are independently a hydrogen atom or is an alkyl group, salts of the ligands including simple salts such as hydrohalogen acids, oxalic acid, and tartaric acid, and m and $m_1$ can be zero or 1. For convenience, these ligands will be referred to as ligand 1.

The basic feature of the BCA of the present invention consists of an internal thiolactone built on the backbone of the strong chelating aminethiol ligand system. The thiolactone moiety provides a reactive functionality to allow attachment of the agent to proteins via stable amide bond formation with free amino groups on proteins. Reaction of the thiolactone in this way releases a previously masked thiol group to complete the coordinate core of the chelating system. The overall effect is the introduction of a strong chelating ligand through a covalent bond to the protein. In the event that the protein or other sensitive biomolecule does not contain an amine group, reaction with a thiol, alcohol or other nucleophilic group will also form a stable bond with the bifunctional chelating ligand.

Since the reactive thiolactone functionality is internal, the BCA of the invention requires no activation prior to coupling. Thus, no byproducts of the reaction are released into solution which might affect protein viability. We have maintained the full coordinating potential of both amine groups for facile complex formation.

The present invention also relates to ligands produced by reacting the foregoing ligands 1 with compounds containing at least one free amino thiol or alcoholate group. For convenience this type of compound will be called ligand 2.

The invention still further relates to coordination complexes made by complexing a metal such as technetium-99m, indium-111 and indium-113 with ligand 2 and to certain diagnostic uses of the resulting complexes.

Metals with which the ligands of the present invention may be complexed include technetium especially Tc-99m, and rhenium especially Re-186, Re-188, indium especially In-111 and In-113m, yttrium, especially Y-90.

Amino, thiol, alcohol and other nucleophile containing compounds contain at least one reactive group. Examples of compounds which contain a primary amino group are benzylamine, human serum albumin, fibrinogen, anticolon carcinoma monoclonal antibody, anti-Rauscher leukemia monoclonal antibody, polyclonal anti-ferritin antibody, peptides, amino acids, natural or synthetic analogs thereof.

Preferably $R^1$ is a hydrogen atom, R" and R"' are methyl groups and m is equal to 0 and $m_1$ is equal to 1.

The term "lower alkyl" denotes alkyl groups such as methyl, ethyl, isopropyl and n-propyl. Higher alkyl groups may be used.

The synthesis of an example of the ligand 1 was accomplished in seven steps as shown in the drawings. The ligand backbone was constructed as described in the literature through diimine formation between ethylenediamine and 2,2'-dithiobis(2-methylpropanal) (2) to yield 3. Synthesis of these starting materials is already known, see Corbin, Journal of Organic Chemistry, Vol. 41, pages 489–491 (1976) and Merz et al., M. Arch. Pharm. Vol. 296, page 427 (1963). Sodium borohydride reduction, while leaving the disulfide bond intact, provides bicyclic amine 4 in 80% yield via intramolecular cyclization of the intermediate mono-imine. See Joshua et al., J. Org. Chem., Vol. 52, page 2447 (1987). This cyclization is advantageous because it permits the differentiation of the two nitrogens for subsequent synthetic elaboration. The bicyclic amine is then alkylated with methyl iodide in the presence of KF/celite (Ando et al., J. Chem. Lett. 45 (1979)), which gives 93% conversion to 5. Reduction of this intermediate with lithium aluminum hydride in refluxing tetrahydrofuran cleaves not only the disulfide bond, but also the transannular C—N bond, affording the open-chained ligand 6 (74% yield, isolated as the di-hydrochloride salt). The thiols are protected as the acid-labile p-methoxybenzyl-thioethers by reaction of dithiol 6 with p-methoxybenzylchloride in an aqueous ethanolic solution of sodium hydroxide to give 7 in 76% yield. Incorporation of the two-carbon side-chain which becomes part of the thiolactone is accomplished through the alkylation of the free base with ethyl bromoacetate, to afford 8, the requisite precursor to the bifunctional chelate, in 55% yield.

The key transformation of precursor 8 to the bifunctional chelating agent is accomplished through hydrolysis with hydrogen fluoride. See Sakakibara et al., Bull. Chem. Soc., Japan, Vol. 40, page 2164 (1967) and Sakakibara et al., Proc. Eur. Peptide Symp., 8th Noordwijk, Neth. 44 (1966). Anhydrous HF is condensed into a Teflon container containing 8 and anisole, present as a free-radical scavenger. After stirring for 1.5 hours in an ice bath, the mixture is allowed to warm to room temperature so that the volatile HF may be flushed carefully into a trap containing excess aqueous potassium hydroxide. Extractive work-up of the residue and short path chromatography on silica provided the thiolactone 1 directly in 70% yield. The isolated material exhibited spectral and analytical data in full agreement with the assigned structure. Infrared spectroscopy showed the carbonyl stretching frequency at 1655 cm$^{-1}$, which is similar to that of six-membered thiolactones reported in the literature, see Korte et al., Chem. Ber., Vol. 94, page 1966 (1961), and did not show evidence of polymerization. Based upon nuclear magnetic resonance ($^1$H, $^{13}$C) studies and the precise elemental analysis obtained for 1, the isolated material is not contaminated with minor products resulting from incomplete hydrolysis of the protecting groups or from hydrolysis of the thioester to the thiol-acid.

APPROACH TO LABELING PROTEINS WITH TECHNETIUM OR RHENIUM

Because proteins possess a large preponderance of weak binding sites for Tc, we chose an approach for labeling that represents a modification of the conventional use of the bifunctional chelate approach. The initial step involves the coupling of the Ligand 1 with the protein. The second step involves formation of a labile Tc-99m complex for example by reduction of [TcO$_4$]$^-$ in the presence of a weak ligand. This weak ligand binds with the metal to form an intermediate complex, which is then used to transfer the metal to ligand 2. That is, the products from the previous steps, i.e. ligand 2 and the intermediate labile complex, are mixed and equilibrated under conditions to allow the transfer of metals such as Tc-99m or Re-186 from the labile complex to the strong chelating agent bound to the protein, i.e. ligand 2 in the process of exchange labeling or transchelation. By proper choice of labile complex, weak binding sites on the protein are not permitted to extract Tc from the partially stabilized reduced Tc, i.e. from the labile complex. [Tc-99m]glucoheptonate can serve as the labile complex in the synthesis of [Tc-99m]DADT complexes by ligand exchange and its incubations with HSA or IgG did not lead to the transfer of reduced Tc to these proteins. Tc-glucoheptonate was therefore chosen for initial evaluation. The use of other labile complexes is quite feasible as well.

More specifically, in the initial step, a compound of formula 1 is coupled with an amine, protein or antibody. Suitable amines, proteins and antibodies include benzylamine (BzA), human serum albumin (HSA), fibrinogen, anticolon carcinoma monoclonal antibody (B72.3), anti-Rauscher Leukemia Monoclonal Antibody (A-RL) and polyclonal anti-ferritin antibody (A-F). The reaction can be carried out at room temperature for as long as needed, usually less than 2 hours at a pH of 7–10. Other pH's for the coupling reaction are possible, as long as the substrate is stable at that particular pH.

In the second step, the alkali metal salt of technetium-99m pertechnetate or Re-186 or Re-188 perrhenate is reacted with a weakly coordinating ligand such as glucoheptonate in the presence of a reducing agent such as stannous chloride or sodium dithionate to form a labile Tc-99m complex. Among the technetium-99m pertechnetate and perrhenate salts are included the alkali metal salts such as sodium salts or ammonium salts, or lower alkyl amine salts.

In the final step, an aliquot of the labile Tc-99m, Re-186 or Re-188 complex was added to the solution of the complex to form a coordination compound.

The invention is further described in the following detailed examples:

Figure 1:
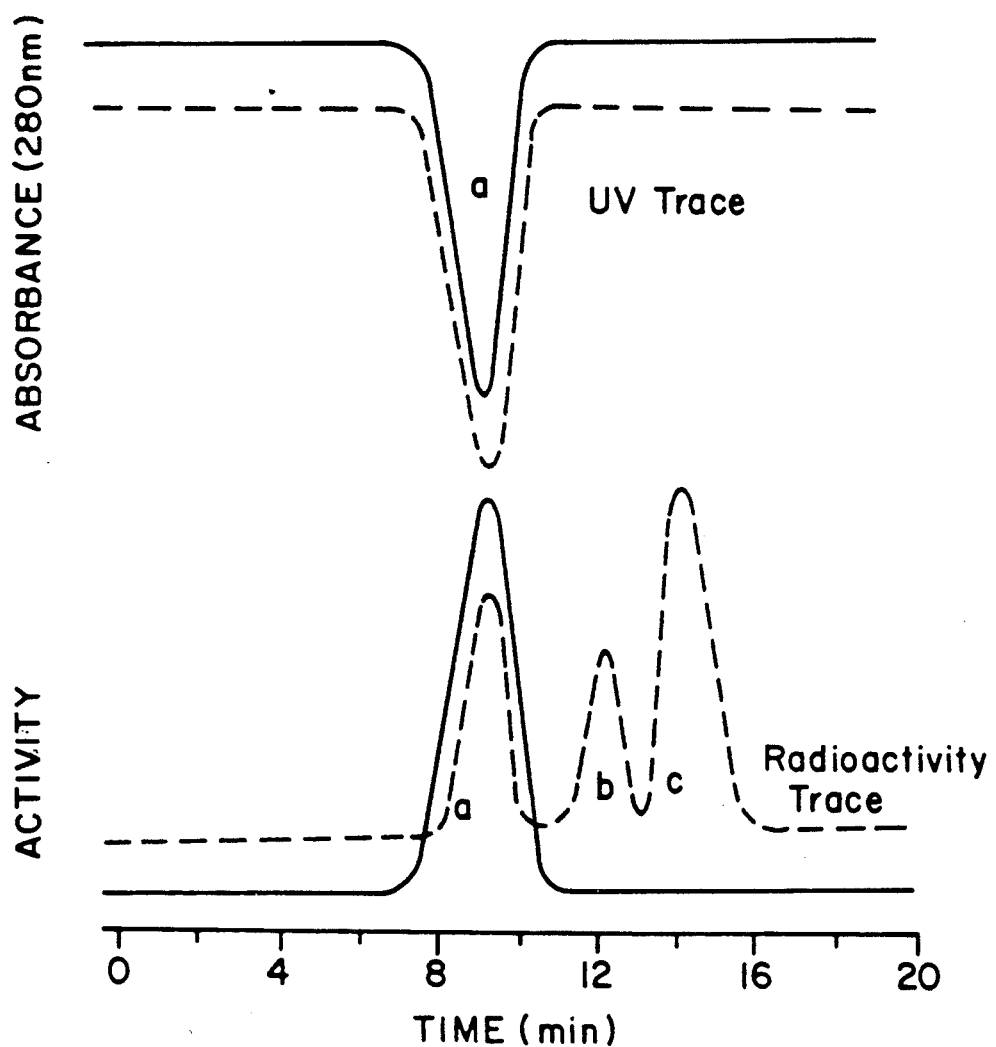
FIG. 1 shows HPLC traces of the purified Tc-99m labeled HSA (- - - -) and Tc-99m-3DADT:HSA (—) incubated at room temperature for 3.5 hours.

DETAILED DESCRIPTION OF PREFERRED EMBODIMENTS SYNTHESIS OF ONE BIFUNCTIONAL CHELATING AGENT COUPLING OF ONE BIFUNCTIONAL CHELATING AGENT WITH A SIMPLE AMINE, PROTEIN AND ANTIBODY

Reaction of BCA with Benzylamine and Subsequent Complexation with Tc-99m.

After the synthesis of BCA (prepared in Examples 1-7), its expected ability to react with amine nucleophiles was evaluated using benzylamine as a model as described in detail below. The reaction proceeded smoothly in solution at room temperature and was practically complete in 3 hours as indicated by TLC. Complexation with Tc-99m via exchange labeling was then investigated. Aliquots of a freshly prepared [Tc-99m] glucoheptonate ("Glucoscan" kit) were added to solutions of the DADT-benzylamine adduct (DADT-BzA). The progress of the reaction was followed by reverse phase high performance liquid chromatography (HPLC) monitored on line by both ultraviolet absorption and radioactivity. Two products, presumably isomers, were formed during labeling with DADT-BzA. Because the labeled protein will behave as a Tc-tagged radiopharmaceutical (Burns et al., 1978) the presence of a mixture of products from the complexation reaction does not detract from the use of the thiolactone BCA. The efficiency of labeling was greater than 90% at ligand concentrations of $10^{-4}$M, and no evidence of contaminating colloidal $TcO_2$ was observed.

As an initial measure of complex stability, the ability of the DADT-BzA ligand to compete with DTPA for reduced Tc was also investigated. Using a DTPA:-DADT-BzA ratio of 120:1, direct or exchange labeling with Tc-99m was explored. Challenge experiments with DTPA were also performed in which the isolated complexes were incubated with 0.1M DTPA. These experiments showed no evidence of the formation of a [Tc-99m]DTPA complex up to 3 hours of incubation. The results indicate that the [Tc-99m]DADT-BzA complexes were more stable than the Tc-99m complex of DTPA, the most frequently used chelate employed in the bifunctional chelate approach.

Coupling of the Bifunctional Chelating Agent, to Human Serum Albumin and Subsequent Labeling with Tc-99m Human serum albumin (HSA) was chosen as the initial model protein to investigate the coupling reaction with proteins and subsequent labeling with Tc-99m. Coupling was investigated at pH 7 and 8 in phosphate buffer using an initial BCA:HSA coupling ratio of 50:1. The coupling reaction proceeded faster at pH 8 than at pH 7 for HSA. This result is consistent with the expectation that the principal nucleophile which attacks the carbonyl center of the thiolactone is the unprotonated $\epsilon$-amino group of lysine. The pKa of this moiety is 10.28 and there would be a greater number of unprotonated amino groups at pH 8 than pH 7. A time dependent coupling of BCA onto HSA was observed, and up to an average of 6 DADT ligands were bound to the protein at either pH 7 or 8.

Both direct (pertechnetate/$Sn^{2+}$) and exchange (preformed [Tc-99m]glucoheptonate) labeling of the coupled proteins were investigated (nDADT:HSA, where n represents the average number of DADT ligands bound to HSA) as compared to the native uncoupled protein (Table 1). There was no detectable protein bound activity during exchange labeling of native, uncoupled HSA compared to 30% labeling efficiency during direct labeling. Exchange labeling efficiently prevented non-specific incorporation of Tc-99m onto HSA. The inability of the native HSA to accept prereduced Tc-99m from [Tc99m]glucoheptonate is an indication of weak Tc-99m binding to the native protein. On the other hand, all the DADT coupled HSA (nDADT:HSA) could be labeled both directly and by exchange. The use of [Tc99m]glucoheptonate afforded proteins labeled only at sites with high affinity for Tc-99m. Since native unmodified protein could not be labeled by exchange from [Tc-99m]glucoheptonate, these high affinity sites must be the DADT chelate sites introduced during coupling. Further, the labeling efficiency increases as the number of chelates per HSA molecule increases (Table 1). At the 3:1 chelate:HSA ratio, the labeling was practically quantitative. Due to the effective increase in the chelating ligand concentration as the chelate:protein ratio increases, the time required for labeling decreases.

TABLE 1

| Labeling Yields of HSA with Technetium-99 m | | | | |
|---|---|---|---|---|
| | DIRECT | | EXCHANGE | |
| Substrate | % | Time (min) | % | Time (min) |
| HSA (unmodified) | 30 | 60 | neg. | 240 |
| 1DADT:HSA | 60 | 30 | 16 | 30 |
| 2DADT:HSA | 70 | 30 | 70 | 30 |
| 3DADT:HSA | 85–100 | 10 | 82–100 | 10 |
| 6DADT:HSA | 80–100 | 10 | 82–100 | 10 |

EXAMPLE 1

Synthesis of 2,2'-Dithiobis(2-methylpropanal) and 1,2-Dithia-5,8-diazacyclodeca-4,8-diene Merz, K. W.; (see) Specker, M. Arch Pharm. 1963, 296, 427.

EXAMPLE 2

Synthesis of 1,1,4,4-tetramethylimidazolino[1,2-d)dithiazepine

The diene obtained in Example 1 (44.5 g, 0.193 mol) was dissolved in EtOH (2.8 L) in a 4 L erlenmeyer flask. Sodium borohydride (17.52 g, 0.46 mol) was added slowly and the mixture was allowed to stir overnight at room temperature. Acetone (100 mL) was added to destroy excess reducing agent. After 15 min., volatile solvents were removed by distillation under reduced pressure to leave a white residue. Aqueous sodium hydroxide (200 mL, 2.5M) was added to the white residue and the mixture was extracted with 4×100 mL ether. The combined ethereal fractions were washed with brine (200 mL), and then dried over anhydrous $Na_2SO_4$. After filtration, the ether was evaporated under reduced pressure to obtain the crude product. The product was purified by short path silica chromatography using ethyl acetate as the solvent, followed by recrystallization from n-pentane. The white crystals were harvested, washed with cold n-pentane, and air dried. The yield of the bicyclic amine product was 36.3 g (80%). mp 63°–64° C., lit. mp 65° C. (Joshua, A. V.; Scott, J. R.; Sondhi, S. M.; Ball, R. G.; Lown, J. W. J. Org. Chem. Vol. 52, page 2447 (1987)). IR (KBr) 3280 $cm^{-1}$ (N—H). $^1$H NMR ($CDCl_3$) δ: $C(CH_3)_2$ 1.23–1.32, m, 12H; N—H 1.9, s, 1H; NC$\underline{H}_2$, NC$\underline{H}$ 2.50–3.60, m, 7H.

$^{13}$C NMR (CDCl$_3$) δ: 18.66, 24.79, 26.42, 28.28, 46.23, 58.56, 66.62, 91.23.

Elemental analysis calculated for C$_{10}$H$_{22}$N$_2$S$_2$: Theory: C, 51.21; H, 9.45; N, 12.00; S, 27 34. Found: C, 51.42; H, 9.17; N, 11.95; S, 27.50.

EXAMPLE 3

Synthesis of
1,1,4,4,7-pentamethylimidazolino[1,2-d]dithiazepine

Procedure 1

To a solution of bicyclic amine (prepared as described above in Example 2) (4 g, 17 mmol) in acetonitrile (40 mL) 50% KF/Celite (6 g, 51 mmol) was added followed by methyl iodide (2.4 mL, 5.47 g, 40 mmol). The mixture was stirred at room temperature for 3 hr and filtered. Volatile solvents were removed by distillation under reduced pressure to produce a wet residue. Aqueous sodium hydroxide (30 mL, 2.5M) was added to the residue and the mixture was extracted with 3×25 mL portions of ether. Additional product was obtained from the celite precipitate by treatment with aqueous NaOH (25 mL, 2.5M) followed by extraction with 3×25 mL portions of ether. The combined ethereal extracts were washed with brine (50 mL). The ether solution was then dried over anhydrous Na$_2$SO$_4$. After filtration, the ether solution was treated at reflux with activated charcoal for 20 min. The charcoal was filtered, and the ether evaporated under reduced pressure. The crude product was purified by short path silica chromatography using 85:15 hexane/ethyl acetate as the solvent. Isolation afforded the methylated product as a clear oil (3.95 g, 93%). bp 121°–122° C. at 2.4 mm Hg pressure. IR (neat) no N—H stretch at 3300 cm$^{-1}$. $^1$H NMR (CDCl3) δ: C(CH$_3$)$_2$ 1.22–1.32, m, 12H; NCH$_3$ 2.48, s, 3H; NCH, NCH$_2$ 2.60–3.10, m, 7H. $^{13}$C NMR (CDCl$_3$) δ: 19.31, 24.41, 26.40, 27.92, 46.06, 54.16, 54.84, 66.88, 100.05.

Elemental analysis calculated for C$_{11}$H$_{24}$N$_2$S$_2$: Theory: C, 53.61; H, 9.00; N, 11.37; S, 26.02. Found: C, 53.60; H, 8.94; N, 11.35; S, 26.00.

Procedure 2

As an alternative to procedure 1, the following procedure was used. To a solution of bicyclic amine (prepared as decribed above in Example 2) 12.32 g, 10 mmol) in benzene (100 mL) methyl iodide (1.25 mL, 2.84 g, 20 mmol) was added. The mixture was refluxed overnight. After cooling, benzene was removed by distillation under reduced pressure. Aqueous NaOH (25 mL, 2.5M) was added to the residue and the mixture extracted with 3×25 mL ether. The combined ether extracts were dried over anhydrous Na$_2$SO$_4$ and then filtered. After removal of the ether by distillation under reduced pressure, the crude product was purified by short path silica chromatography using 85:15 hexane/ethyl acetate as the solvent. The yield was 1.66 g (67%). The product was similar in all respects to that obtained from the preceding procedure.

EXAMPLE 4

Synthesis of
2,2,4,9,9-pentamethyl-4,7-diaza-1,10-decanedithiol

To a stirred solution of N-methyl bicyclic amine (as prepared in Example 3) (15 g, 60.62 mmol) in a dry THF (100 mL) under a slow stream of nitrogen, LiAlH$_4$ (5 g, 132 mmol) was added in small portions. The mixture was refluxed for 2 hr and then cooled to room temperature. The reaction was quenched by slow dropwise addition of saturated NH$_4$Cl while being externally cooled in an ice bath. The mixture was then quickly triturated with 4×50 mL portions of ethanol into a vessel containing one equivalent of 3N HCl. The pH of the mixture was adjusted to 3–4 and volatile solvents removed by distillation under reduced pressure. Water (50 mL) was added to the residue and the pH adjusted to 8 with aqueous sodium hydroxide (2.5M). The mixture was then extracted 3×60 mL with ether. The combined ethereal extracts were dried with anhydrous Na$_2$SO$_4$ and filtered. The ether solution was concentrated to about 50 mL under reduced pressure and then passed over a 50 g silica column, the product being eluted with ether. The ether solution was evaporated under reduced pressure and the residue dried under high vacuum for 1 hr. For long-term storage, the free base was converted to the hydrochloride salt by adding ethanol (30 mL) to the residue and the solution saturated with dry HCl gas. The resulting warm solution was cooled to room temperature and the product precipitated with ether, filtered and washed with ether, then dried under high vacuum to afford a white solid (14.54 g, 74%). IR (neat, free base) 3300 cm$^{-1}$ (N—H), 2540 cm$^{-1}$ (S—H). $^1$H NMR (free base, CDCl$_3$) δ: —C(CH$_3$)$_2$ 1.35, 1.37, 2s 12H; N—H and S—H 1.90 broad 3H; N—CH$_3$ 2.38, s 3H; N—CH$_2$ 2.48, 2.62, 2.71, 3s 8H. $^{13}$C NMR (CDCl$_3$) δ: 30.48, 44.63, 45.26, 46.24, 48.40, 59.94, 63.74, 72.21.

Elemental analysis calculated for C$_{11}$H$_{26}$N$_2$S$_2$.2HCl: Theory: C, 40.85; H, 8.73; Cl, 21.93; N, 8.66; S, 19.83. Found: C, 40.92; H, 8.73; Cl, 21.94; N, 8.61; S, 19.75.

Example 5

Synthesis of
2,2,4,9,9-pentamethyl-4,7-diaza-1,10-[bis-p-methoxybenzyl]-1,10-dithiadecane Aqueous sodium hydroxide (50 mL, 2.5M) was added to a stirred solution of N-methyl thiol (prepared as described above in Example 4) (4 g, 12.4 mmol) in ethanol (60 mL) followed by neat p-methoxybenzyl chloride (8.8 g, 56.19 mmol). Stirring was continued for 1 hr and most of the ethanol distilled under reduced pressure. The mixture was then extracted 3×50 mL with ether. The combined ethereal solutions were dried with anhydrous Na$_2$SO$_4$. After filtration the ether was evaporated and the oily residue was redissolved in ethanol (10 mL). The pH of the mixture was adjusted to 2–3 with HCl dissolved in ethanol (saturated). The warm mixture was cooled to room temperature and the product was precipitated with ether. The precipitate was filtered, and washed with ether to yield a white di-HCl salt (6.9 g, 76%). For subsequent use, the free base was regenerated by treatment of the di-HCl salt with 2.5M NaOH followed by extraction with ether. IR (free base, neat) 3300 cm$^{-1}$ (N—H). $^1$H NMR (free base, CDCl3) δ: C(CH$_3$) 1.32, s, 12H; NH (with H$_2$O) 1.6, b; NCH$_3$ 2.36, s, 3H; NCH$_2$ 2.50, 2.57, 2.61, 3s, 8H; Bz—CH$_2$ 3.66, 3.73, 2s 4H; OCH$_3$ 3.77, s, 6H; Ar—H 6.75, 6.85, 7.19, 7.29, AB q, 8H. $^{13}$C NMR (free base, CDCl$_3$) δ: 26.07, 26.93, 27.24, 32.05, 44.79, 46.87, 47.63, 47.80, 48.47, 55.11, 59.96, 60.11, 64.53, 69.38, 113.78, 129.83, 130.38, 158.40.

Elemental analysis calculated for C$_{27}$H$_{42}$N$_2$O$_2$S$_2$: Theory: C, 66.08; H, 8.63; N, 5.71; S, 13.07. Found: C, 65.99; H, 8.64; N, 5.68; S, 13.02.

EXAMPLE 6

Synthesis of
2,2,4,9,9-pentamethyl-4,7-diaza-7-(ethylcarboxymethyl)-1,10-(bis-p-methoxybenzyl)1,10-dithiadecane A solution of N-methyl protected thiol (prepared as described in Example 5) as the free base (20 g, 40.75 mmol) and ethyl bromoacetate (34.03 g, 203.76 mmol) in acetonitrile (75 mL) was heated at 44° C. for 3 hr. Volatile solvents were removed by distillation under reduced pressure. Water (20 mL) was added to the residue and the pH of the mixture adjusted to 8-9 with aqueous NaOH (2.5M), and then extracted with 3×50 mL aliquots of ether. The combined ethereal solution was dried with anhydrous $Na_2SO_4$. After filtration the ether was evaporated under reduced pressure. Excess ethylbromoacetate was removed via a Kugelrohr apparatus at room temperature and 0.5 mm Hg pressure. The residue was then chromatographed on a short path silica column with 89.5:10:0.5 hexane/ethyl acetate/triethylamine as solvent to yield a clear oil (13 g, 55%). IR (neat) 1730 cm$^{-1}$ (O=C—OEt) $^1$H NMR (CDCl$_3$) δ: $CH_2CH_3$, $C(CH_3)$, 1.16-1.33, m, 15H; NCH$_3$ 2.34, s, 3H; NC$\underline{H}_2$ 2.47-2.79, m, 8H; NCH$_2$CO 3.56, s, 2H; Bz—C$\underline{H}_2$ 3.71, s, 4H; OCH$_3$ 3.77, s, 6H; OC$\underline{H}_2$CH$_3$, 4.15, q, 2H; Ar—$\underline{H}$ 6.75, 6.86, 7.18, 7.28, AB q, 8H. $^{13}$C NMR (CDCl$_3$) δ: 14.22, 26.71, 26.88, 32.14, 45.20, 47.62, 47.91, 54.54, 55.14, 56.74, 59.32, 59.97, 66.74, 113.34, 129.37, 130.35, 153.45, 171.94.

Elemental analysis calculated for $C_{31}H_{48}N_2O_4S_2$: Theory: C, 64.54; H, 8.39; N, 4.86; S, 11.12. Found: C, 64.48; H, 8.42; N, 4.84; S, 11.05.

EXAMPLE 7

Synthesis of Thiolactone Bifunctional Chelating Agent

Anhydrous hydrogen fluoride (5.85 g, 308 mmol) was condensed into a 100 mL teflon round bottom flask containing the precursor prepared in Example 6 (2.33 g, 4.04 mmol) and anisole (0.93 g, 8.48 mmol) and externally cooled by a dry ice/acetone bath. After addition was complete, the mixture was stirred for 1.5 hr in an ice both (0° C.) under a positive pressure of nitrogen. Most of the HF was then flushed with a stream of nitrogen into a KOH trap. Water (10 mL) was added to the residue and the pH raised to 2-3 with aqueous NaOH (2.5M). The mixture was then washed 4×15 mL with ether and the ether fractions discarded. The pH of the aqueous layer was adjusted to 8 and the mixture extracted 3×20 mL with ether. This ether layer was dried with anhydrous Na$_2$SO$_4$ for 30 min, filtered, and evaporated under reduced pressure to leave a crude oily residue. The mixture was chromatographed on a short path silica column using 90:10 hexane/ethyl acetate to yield the target thiolactone bifunctional chelating agent, (0.82 g, 70%). IR (neat) 1655 cm$^{-1}$ (O=C—SR). $^1$H NMR (CDCl3) δ: SC(CH$_3$)$_2$ 1.32, s, 6H; COSC(CH$_3$)$_2$ 1.48, s, 6H; NCH$_3$ 2.41, NCH$_2$ 2.47, 2.68, 2s, 8H; NCH$_2$CO 3.32, s, 2H. $^{13}$C NMR (CDCl$_3$) δ: 29.89, 30.46, 45.20, 46.23, 47.65, 56.00, 57.74, 65.14, 72.22, 199.00.

Elemental analysis calculated for $C_{13}H_{26}N_2OS_2$: Theory: C, 53.94; H, 8.70; N, 9.68; S, 22.15. Found: C, 53.82; H, 8.79; N, 9.60; S, 22.04.

EXAMPLE 8

Synthesis of 2,2,4,9,9-Pentamethyl 4,7-diaza-7-[benzylamidomethyl]-1,10-[bis-p-methoxybenzyl]-1,10-dithiadecane, (diaminedithiol-Benzylamine Adduct, DADT-BzA)

Under an atmosphere of nitrogen, a solution of the thiolactone bifunctional chelating agent, (200 mg, 0.691 mmol) and benzylamine (110 mg, 1.02 mmol) in acetonitrile (5 mL) was stirred at room temperature for 3 hours. The acetonitrile was removed by distillation under reduced pressure and the residue was chromatographed on silica preparative plates (2×2000 μ) using 60:40 hexane/ethyl acetate as a solvent. The yield of desired product was 222 mg (81%). The product was kept as the di-HCl salt. IR (free base, neat) 3260, 3160 cm$^{-1}$ (—CON—H). $^1$H NMR (free base CDCl$_3$) δ: $C(CH_3)_2$ 1.20, 1.28, 2s, 12H; S—$\underline{H}$ 1.55, broad, 2H; N—$\overline{CH}_3$ 2.3, s, 3H; N—CH$_2$ 2.34(s), 2.67(m), 8H; NC$\underline{H}_2$C=O 3.38, s, 2H; NC$\underline{H}_2$—C$_6$H$_5$ 4.46, 4.54, m. 2H; $\overline{C_6H_5}$ 7.31, s, 5H; CON$\underline{H}$ 7.8, broad, 1H.

Elemental analysis calculated for $C_{20}H_{35}N_3OS_2$ 2HCl: Theory: C, 51.05; H, 7.93; Cl, 15.07; N, 8.93; S, 13.63. Found: C, 50.27; H, 8.05; Cl, 14.71; N, 8.50; S, 13.26.

Corrected for 0.5H$_2$O: C, 51.23; H, 7.92; Cl, 14.99; N, 8.66; S, 13.51.

In a similar fashion, reaction with lysine analogs was accomplished.

EXAMPLE 9

Technetium-99m Labeling Of the Thiolactone BCA-Benzylamine Adduct (DADT-BzA).

Direct Labeling

To a solution of DADT-BzA (1 mg) in phosphate buffer (0.5 mL, 0.1M, pH 7), a saline solution of [$^{99m}$TcO$_4$]- (0.4 mL, 5 mCi) was added followed by SnCl$_2$ solution (0.1 mL, 2-3 mg SnCl$_2$.2H$_2$O/10 mL EtOH). The mixture was vortexed for 1 min after each addition. After 30 min incubation at room temperature the mixture was analyzed by reverse phase HPLC using an Alltech C-18 Econosil TM column (6.5×250 mm). The HPLC conditions were 90:10 MeOH/0.1M ammonium formate solution at a flow rate of 8 mL/min.

Exchange Labeling

A saline solution of [$^{99m}$TcO$_4$]- from the generator (20-50 mCi, 3 mL) was added to a vial of "Glucoscan" kit (containing sodium glucoheptonate and SnCl$_2$), mixed well and allowed to stand for 15 min. Aliquots of this mixture containing the labile [$^{99m}$Tc]glucoheptonate complex were added to solutions of DADT-BzA to give final ligand concentrations of 10$^{-4}$ and 10$^{-3}$M in a total volume of 1 mL. The appearance of products and the disappearance of the labile $^{99m}$Tc complex were followed with the same chromatographic system as for the direct labeling. The $^{99m}$Tc labeled DADT-BzA was designated as [$^{99m}$Tc]DADT-BzA.

Initial Evaluation of the Novel Bifunctional Chelate for Protein Labeling

EXAMPLE 10

Coupling of the Thiolactone Bifunctional Chelating Agent, to Human Serum Albumin, (HSA)

A solution of HSA (2 ml, 50 mg/ml, 1.5 mmol) in phosphate buffer (0.1M, pH 7 or 8 as required) was added to a vial containing the thiolactone bifunctional chelating agent (22 mg, 75 mmol). The mixture was vortexed to an emulsion and allowed to stand at room temperature with occasional mixing. At every hour for 6 hr and finally at 24 hr incubation time, aliquots of the mixture (0.25 ml) were removed after thorough mixing. Unbound ligand was separated from protein bound ligand by gel filtration HPLC using a Waters Protein Pak 300SW column equipped with a precolumn filter using phosphate buffer (0.1M, pH 7, 2 ml/min) as eluent. The eluent was monitored at 280 nm and the protein fraction was collected. The concentration of protein was determined spectrophotometrically at 280 nm by comparison to a standard curve. The increase in free thiol concentration of the isolated modified protein was then determined using Ellman's assay for thiols. The standard curve for comparison in this assay was generated using 2,2,4,9,9-pentamethyl-4,7-diaza-1,10-decanedithiol, a simple N-methyl derivative of the diaminedithiol ligand, (1–60 mM) to determine the concentration of thiol groups on the modified protein. From these known concentrations of free thiol and protein, the average number of chelate groups/protein molecule was calculated. The course of the reaction was followed by determination of the number of chelate groups per protein molecule as a function of incubation time and pH. The BCA coupled HSA were designated nDADT:HSA where n denotes the average number of diaminedithiol (DADT) chelating groups per HSA molecule.

EXAMPLE 11

Direct Labeling of HSA With $^{99m}$Tc

Aliquots of a saline solution of [$^{99m}$TcO$_4$]-(0.1 ml, 3–5 mCi) were added to samples of protein solutions (1 ml, 2.5–5 mg/ml) of coupled (nDADT:HSA) or of unmodified HSA in phosphate buffer (0.1M, pH 7), followed by a solution of SnCl$_2$ in 0.05M HCl (0.1 ml, 100 mg SnCl$_2$ 2H$_2$O/ml). These reactions, final pH 7, were thoroughly mixed and allowed to stand at room temperature. At different time intervals between 1 and 240 min, the mixtures were analyzed by gel filtration HPLC using phosphate buffer (0.1M, pH 7, 1 ml/min) as eluent.

Exchange Labeling of HSA with $^{99m}$Tc

A saline solution of [$^{99m}$TcO$_4$]- (3–4 ml, 20–40 mCi) was added to glucoheptonate ("Glucoscan") kit, mixed thoroughly and allowed to stand for 15 min at room temperature. Aliquots (0.2 mL, 5 mCi) of this mixture were added to HPLC isolated samples of nDADT:HSA or unmodified HSA (1 ml, 2.5–5 mg/ml) in phosphate buffer (0.1M, pH 7). The mixtures were vortexed thoroughly, allowed to stand at room temperature, and aliquots analyzed periodically by gel filtration HPLC as described above for the direct labeling procedure.

IN VITRO AND IN VIVO EVALUATION OF LABELED PRODUCTS

Summary

As a measure of stability of the labeled HSA molecules, HPLC purified products were incubated at room temperature. For HSA labeled without the use of the BCA, hydrolyzed reduced Tc-99m and [TcO$_4$]$^-$ were formed (FIG. 1). These decomposition products account for 66% of the label at 3.5 hours incubation. These species may be the result of disproportionation of reduced Tc-99m to the more stable oxidation states of Tc (IV and VII) due to the inability of native HSA to stabilize the reduced Tc-99m or the reoxidation and hydrolysis of reduced Tc-99m. On the other hand, the Tc-99m labeled modified HSA (Tc-99m-nDADT:HSA) showed no signs of decomposition under the same conditions. Therefore, the use of the DADT chelating group to coordinate Tc resulted in products that were more stable.

Figure 2B:
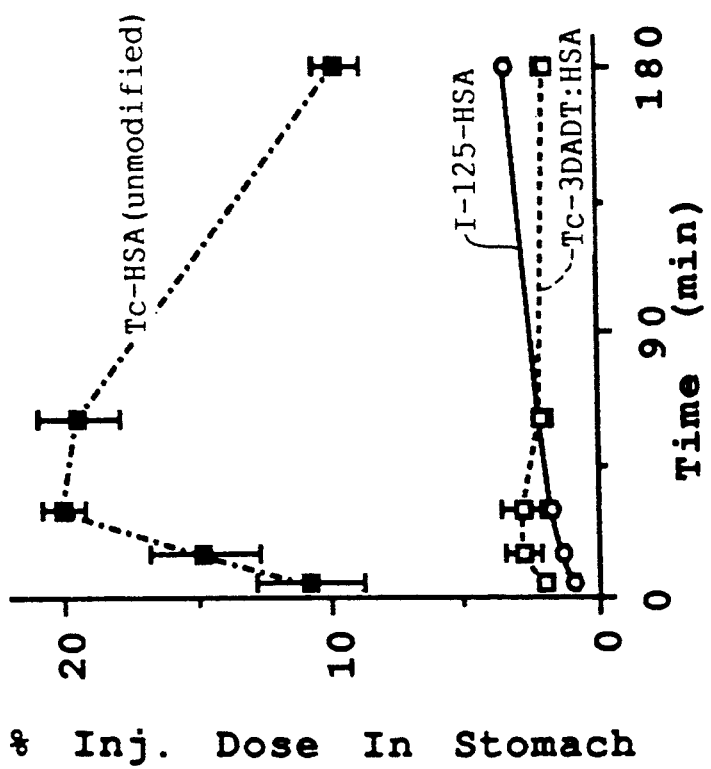
FIG. 2A shows blood retention of labeled HSA in normal mice and FIG. 2B shows stomach accumulation of labeled HSA in normal mice.
Figure 2A:
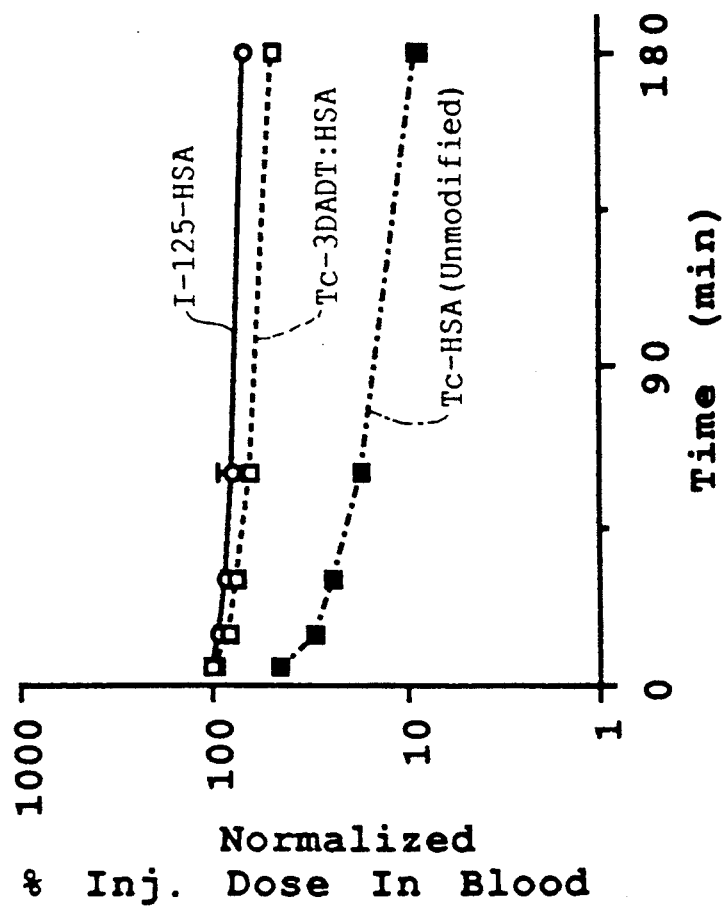

In vivo evaluation of labeled HSA is simplified because the level of radioactivity in the blood is a measure of stability and viability. Any loss of the Tc label or denaturation of the labeled protein will be observed as low blood retention and abnormal accumulation of radioactivity in organs such as stomach, kidney, or liver (Pettit et al., 1978). Biodistribution of the Tc-99m labeled HSA products were compared with I-125 labeled HSA in male CD-1 mice. The behavior of the Tc-99m-nDADT:HSA (n=1–6) were similar in these in vivo studies and are typified by Tc-99m-3DADT:HSA in FIGS. 2A and 2B. The labeled HSA showed high blood retention as expected; but, there was lower initial retention and faster clearance of the label in blood for Tc-99m-HSA (unmodified) than for Tc-99m-nDADT:HSA. The early retention of the label in the blood was similar for Tc-99m-nDADT:HSA and the I-125-HSA. The high blood retention of the labeled HSA is indicative of the viability of the labeled products. The small differences in clearance between the Tc-99m-nDADT:HSA and I-125-HSA at the longer time points may be due to differences in the handling of the respective labels once significant metabolism of the protein has occurred.

Figure 3:
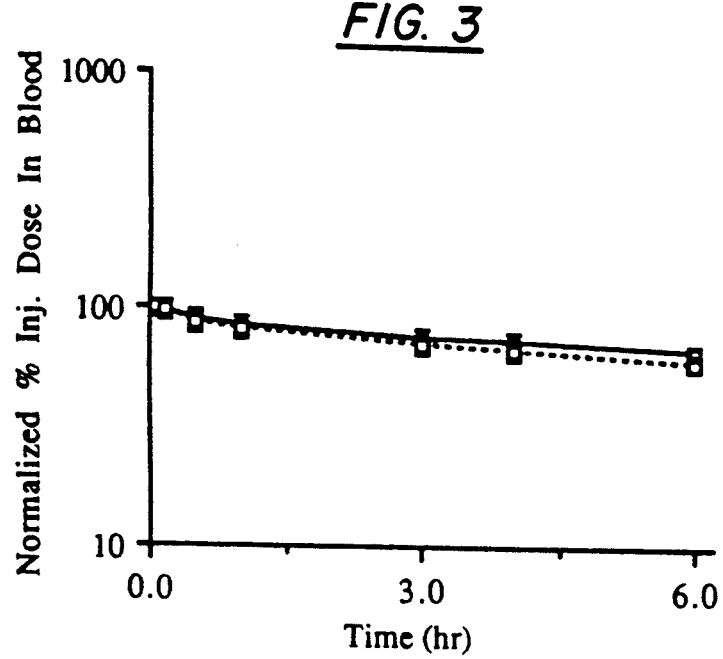
FIG. 3 shows blood retention of Tc-99m and I-125 labeled HSA in rabbit.

In the stomach, the Tc-99m-HSA (unmodified) showed a high uptake (up to 20% of the injected dose by 30 min, (FIG. 2B) similar to the known accumulation of [TcO$_4$]$^-$. This high stomach uptake without accompanying high liver uptake is indicative of the reoxidation of bound Tc-99m in vivo rather than hydrolysis of the reduced Tc-99m or denaturation of the labeled HSA. Reduced, hydrolyzed Tc-99m would have accumulated in the liver (Pettit et al., 1978). The total stomach accumulation of Tc-99m-nDADT:HSA were similar to I-125-HSA <4.5% ID/organ). However, there was a difference in the shape of the time-activity curves for Tc-99m-labeled proteins vs the I-125-HSA. This may be due to the accumulation of deiodinated HSA in the stomach with time reflecting differences in the handling of the two labels following protein metabolism. There were no significant differences in the accumulation of the labeled HSA (Tc-99m or I-125) in the other organs. Liver accumulation was low and this confirmed the in vivo viability of the labeled products. The blood retention of Tc-99m-3DADT:HSA was also compared to I-125-HSA in the rabbit (FIG. 3). Up to six hours postinjection, there was practically no difference in these two species which confirms the stability and viability of the Tc-99m labeled HSA in vivo.

EXAMPLE 12

Biodistribution of Radiolabeled HSA in Mice

The stability of label and the viability of the $^{99m}$Tc-labeled HSA products in vivo were assessed by studying the biodistribution of [$^{99m}$Tc]-labeled HSA and [$^{99m}$Tc]nDADT:HSA (N=1, 2, 3, and 6) as compared to [$^{125}$I]-labeled HSA in mice. The temporal distribution of [$^{99m}$Tc]- and [$^{125}$I]-radioactivity in blood stomach, liver, kidneys, and intestines of male CD-1 mice were determined as follows: HPLC purified [$^{125}$I]-labeled HSA, [$^{99m}$Tc]-labeled HSA and [$^{99m}$Tc]nDADT:HSA (n=1, 2, 3, and 6) were approximately diluted to 10 μCi/ml. Aliquots of the diluted samples (0.2 ml, 2 μCi) were injected through the tail vein. At 5, 15, 30, 60 and 180 min postinjection, groups of six mice were killed by cervical dislocation and the organs of interest were removed by dissection and weighed. Tissue radioactivity was determined using an automated scintillation well counter with a 100 to 180 KeV window. The per cent injected does per gram of wet tissue per organ was calculated by comparison to standard dilutions of the injected dose and corrected for decay.

EXAMPLE 13

Blood Retention of Radiolabeled HSA in Rabbits

Three rabbits were injected through the left ear vein with a mixture of HPLC purified [$^{125}$I]-labeled HSA and [$^{99m}$Tc]3DADT-HSA (50 μCi each). At 5, 15, 30, 60, 180 and 360 min postinjection, 0.5 ml blood samples were drawn from the contralateral ear. The technetium-99m radioactivity in the samples was measured using an automated scintillation well counter with a 100 to 180 KeV window as described above. After a three day, 12 half-lives, decay period for the [$^{99m}$Tc]-radioactivity, the [$^{125}$I]-radioactivity in the samples was measured using the automated scintillation well counter with a 20 to 80 KeV window.

Three intact IgG antibodies, anti-colon carcinoma monoclonal antibody (B72.3), an anti-Rauscher leukemia monoclonal antibody (A-RL), and a polyclonal anti-ferritin antibody (A-F), were used to evaluate the utility of the approach for labeling. sensitive antibodies. Coupling was performed at pH 9 at different coupling ratios at room temperature. The results indicate (Table 2) that up to 6.8 DADT ligands could be introduced to intact IgG antibodies under the conditions used here. The coupling yields obtained with B72.3 were lower because the protein concentrations used here were five times lower than used for the other antibodies. Increased protein concentrations would allow the use of lower BCA:Protein coupling ratios as well as lower reaction temperatures if needed.

TABLE 2

Coupling of BCA 1 to IgG Antibodies:
A) Anti-Colon Carcinoma Monoclonal Antibody (B72.3);
B) Polyclonal Anti-Ferritin Antibody;
C) Anti-Rauscher Leukemia Monoclonal Antibody.

|  | BCA:Protein Ratio | Temp. | Time (hours) | DADT:Protein Ratio |
|---|---|---|---|---|
| A) | 50:1 | rt | 2 | 0.5:1 |
|  | 100:1 | rt | 1 | 1.0:1 |
|  | 100:1 | rt | 2 | 3.0:1 |
| B) | 10:1 | rt | 2 | 1.5:1 |
|  | 25:1 | rt | 2 | 2.1:1 |
|  | 50:1 | rt | 2 | 4.0:1 |
|  | 100:1 | rt | 2 | 4.7:1 |
| C) | 10:1 | rt | 1 | 1.5:1 |
|  | 25:1 | rt | 1 | 2.5:1 |
|  | 100:1 | rt | 1 | 2.9:1 |
|  | 100:1 | rt | 2 | 6.8:1 |

Labeling IgG Antibodies with $^{99m}$Tc.

Exchange labeling of the antibodies was performed at pH 7 at 37° C. by the addition of the [Tc-99m]glucoheptonate solution to lyophilized coupled protein. The extent of labeling was followed by gel filtration HPLC. As with HSA, exchange labeling prevented the incorporation of Tc to the uncoupled protein as exemplified for the polyclonal anti-ferritin antibody (Table 3).

TABLE 3

Exchange Labeling of Polyclonal Anti-ferritin Antibody

| DADT:Protein Ratio | Protein (mg) | Time (hours) | % Prot bound Tc-99 m |
|---|---|---|---|
| 0:1 | 1.1 | 0.5 | not detectable |
|  |  | 1.0 | not detectable |
|  |  | 1.5 | not detectable |
|  |  | 2.0 | not detectable |
| 1.1:1 | 0.9 | 0.5 | 34.1 |
|  |  | 1.0 | 57.6 |
|  |  | 1.5 | 71.8 |
|  |  | 2.0 | 77.7 |
| 2.0:1 | 1.6 | 0.5 | 73.7 |
|  |  | 1.0 | 85.6 |
|  |  | 1.5 | 88.3 |
|  |  | 2.0 | 92.0 |
| 2.8:1 | 0.95 | 0.5 | 80.2 |
|  |  | 1.0 | 89.6 |
|  |  | 1.5 | 100 |
|  |  | 2.0 | 100 |
| 4.0:1 | 1.1 | 0.5 | 100 |
|  |  | 1.0 | 100 |
|  |  | 1.5 | 100 |
|  |  | 2.0 | 100 |

Specific details of the coupling and subsequent labeling procedures are given below with the B72.3 antibody as an example.

EXAMPLE 14

Coupling of the Bifunctional Chelating Agent to the Monoclonal Antibody, B72.3

Coupling of monoclonal antibody B72.3 was performed at a BCA (prepared in Examples 1-7) to protein ratio of 100 to 1 at room temperature. The reactions were performed in borate buffer (pH 9, 25 mM) containing saline (150 mM NaCl). From our initial investigations this buffer system was previously shown to be more efficient than phosphate buffer at pH 8 for coupling IgG. The thiolactone bifunctional chelating agent was added as a solution in DMF (0.1 ml) to the protein solution (1.5-2 mg/0.9 ml). After 2 hr incubation, the protein bound ligand was separated from free ligand using disposable PD-10 columns eluted with a phosphate-citrate buffer at pH 7 (2 mM phosphate, 10 mM citrate with 150 mM NaCl). The number of ligand molecules per protein molecule was calculated as described above. The coupled B72.3 were designated nDADT:B72.3 where n denotes the average number of chelates per protein molecule. The isolated coupled proteins were lyophilized and stored in the freezer until the labeling experiments were performed.

EXAMPLE 15

Exchange Labeling of B72.3 with $^{99m}$Tc

[$^{99m}$Tc]glucoheptonate from the "Glucosan" kit was used as the source of reduced Tc. The [$^{99m}$Tc]glucoheptonate solution (0.2 ml, 5 mCi) was added to the lyophilized coupled (nDADT:B72.3 or unmodified protein (0.5-1 mg) and incubated at 37° C. The lyophilized unmodified protein was directly labeled at pH 7 by adding buffer (2 mM phosphate, 10 mM citrate, and 150 mM NaCl, pH 7.0, 0.15 ml) followed by a stannous chloride solution prepared in the same buffer (0.2 mg SnCl$_2$ 2H$_2$O/ml buffer, 0.05 ml). The mixtures were analyzed by gel filtration HPLC using a Waters Protein Pak 300SW column eluted with the above buffer at a flow rate of 1 ml/min.

EXAMPLE 16

In Vitro Stability of $^{99m}$Tc Labeled B72.3

The stability of the $^{99m}$Tc-labeled protein in vitro in human plasma was assessed for the modified protein containing an average of 2 chelating ligands per protein molecule ([$^{99m}$Tc]2DADT:B72.3, labeled by exchange) and for the unmodified protein ([$^{99m}$Tc]-labeled B72.3, labeled directly). The labeled proteins were isolated by gel filtration chromatography and incubated with human plasma (50/50 v/v: plasma/eluent) at 37° C. over a period of 20 hr. Aliquots of the incubation mixture were analyzed by gel filtration HPLC using the system described above for analysis of the labeling reactions.

There was only one radioactive peak congruent with an ultraviolet peak at 8.9 minutes retention time corresponding to IgG for the Tc-99m-2DADT:Antibodies. There was therefore no evidence of transchelation to any serum proteins or decomposition of the labeled antibody. On the other hand, incubation of antibody directly labeled without the use of the thiolactone bifunctional chelating agent (Tc-99m-Antibodies) showed the same radioactive decomposition products (47%) as shown for HSA (vide supra).

EXAMPLE 17

Biodistribution of $^{99m}$Tc Labeled B72.3

The in vivo stability of the [$^{99m}$Tc]2DADT:B72.3 monoclonal antibody containing an average of 2DADT ligand per protein molecule was assessed by studying its biodistribution in normal male CD-1 mice. The protocol followed was as described for the radiolabeled HSA except each mouse was injected through the tail vein with a solution of the [$^{99m}$Tc]2DADT:B72.3 (0.2 ml, 10 μCi) and groups of three mice were killed at postinjection intervals of 5 min, 2 hr, and 18 hr.

Table 4 indicates that the low concentration of activity in the stomach, kidneys, and intestines, coupled with the high blood retention are indicative of high in vivo stability of the label. These results are comparable to those obtained by Arano and coworkers on their Tc-99m-CE-DTS-IgG antibody, except that this system showed a faster clearance of activity from the liver and overall lower activity concentration in the stomach, an indication of a high extent of stability.

TABLE 4

Biodistribution of [Tc-99 m]2DADT:B72.3 Monoclonal Antibody in Mice (% Injected Dose/gm (Mean ± SD for 3 Determinations))

| Organ | 5 minutes | 2 hours | 18 hours |
|---|---|---|---|
| Blood | 39.67 ± 1.60 | 23.88 ± 3.87 | 10.25 ± 2.22 |
| Brain | 1.12 ± 0.26 | 0.63 ± 0.21 | 0.36 ± 0.09 |
| Heart | 5.63 ± 0.87 | 5.43 ± 0.57 | 2.79 ± 0.67 |
| Lungs | 12.97 ± 3.40 | 8.24 ± 2.0 | 4.26 ± 1.18 |
| Liver | 10.67 ± 1.86 | 6.10 ± 1.37 | 3.27 ± 0.75 |
| Spleen | 4.31 ± 0.63 | 3.25 ± 0.88 | 2.23 ± 0.79 |
| Kidneys | 5.97 ± 0.25 | 8.92 ± 0.59 | 6.49 ± 0.46 |
| Stomach | 1.31 ± 0.39 | 1.40 ± 0.36 | 0.71 ± 0.18 |
| Muscle | 0.81 ± 0.25 | 1.14 ± 0.21 | 0.88 ± 0.26 |
| Intestines | 1.15 ± 0.34 | 2.83 ± 0.34 | 1.25 ± 0.33 |

EXAMPLE 18

The In Vitro Viability of the Coupled and Labeled A-RL Antibody

The in vitro viability of the DADT-coupled and Tc-99m labeled anti-Rauscher erythroleukemia monoclonal antibody, A-RL, were investigated in in vitro binding assays. Table 5 shows that for the coupled antibody, up to an average of 2.9 DADT ligands can be introduced to the antibody without significantly affecting the in vitro viability of the antibody.

TABLE 5

In vitro Binding Studies of Coupled Anti-Rauscher Leukemia MoAb (A-RL)

| Substrate | % Maximum Binding of Control (Uncoupled A-RL) |
|---|---|
| Specific Ab (A-RL) | |
| 1.5 DADT:A-RL | 95.3 |
| 2.5 DADT:A-RL | 95.4 |
| 2.9 DADT:A-RL | 93.1 |
| 6.8 DADT:A-RL | 87.1 |
| Non-Specific IgG | |
| 1.7 DADT:NS-IgG | 0.6 |
| 6.3 DADT:NS-IgG | 0.4 |

Figure 4:
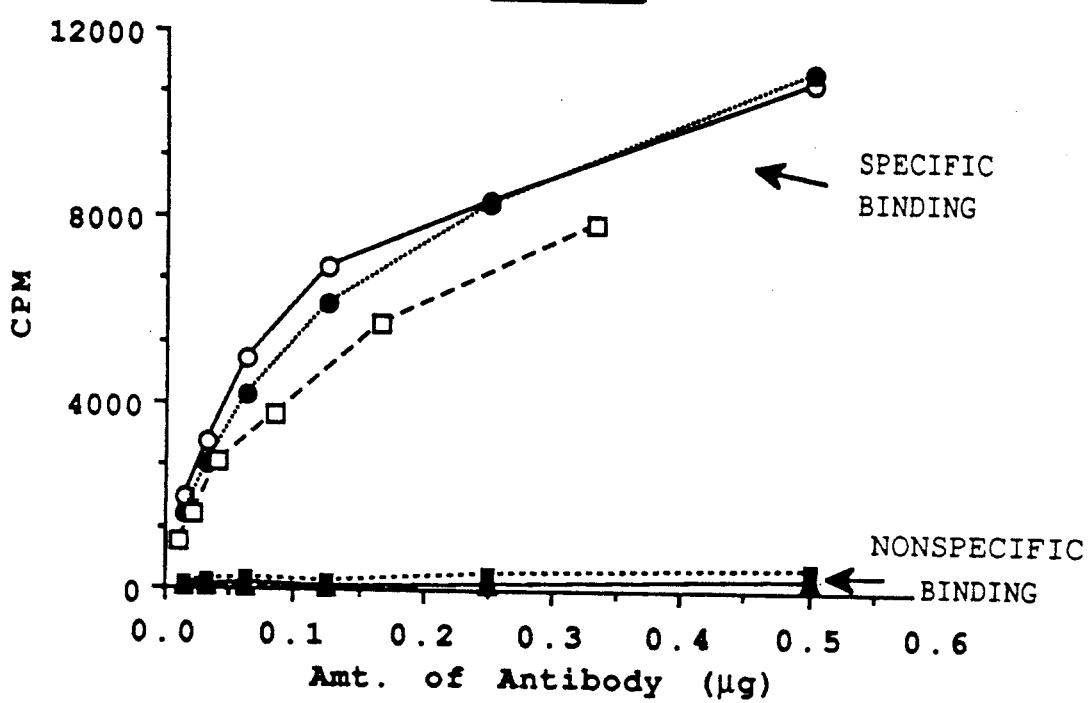
FIG. 4 shows in vitro binding studies of coupled anti-Rauscher Leukemia MoAb (A-RL).
Figure 5:
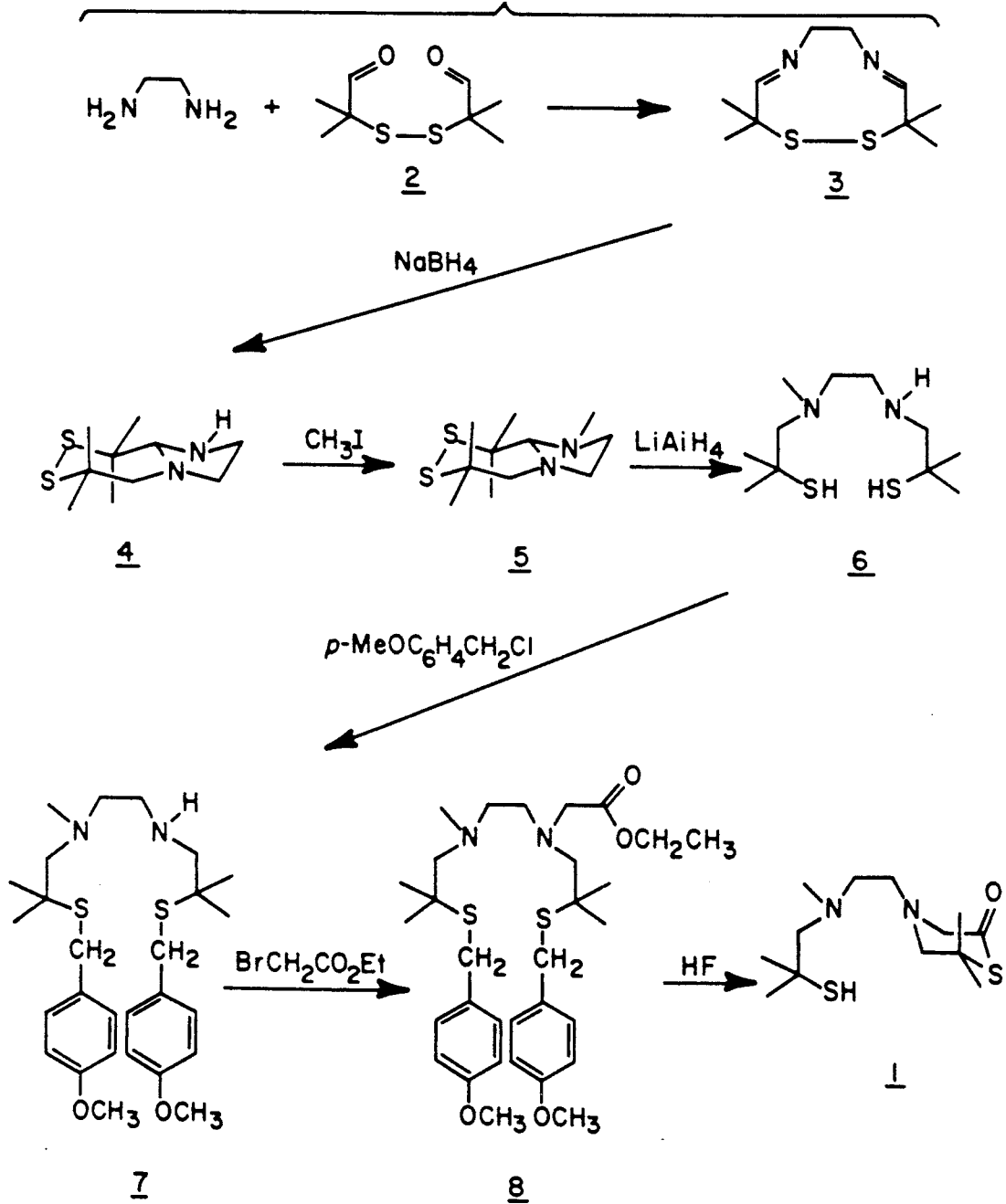
FIG. 5 shows synthesis of one bifunctional chelating agent.

FIG. 4 shows that the labeled A-RL antibodies maintained high binding capacity compared to control non-specific human IgG. Again, there was no significant difference between the antibodies containing up to the DADT ligands per protein molecule. The labeled A-RL containing an average of 6.8 DADT ligands per antibody molecule showed a slightly lower binding capacity. However, on the whole, high binding capacity of the Tc labeled specific antibodies by this methodology was observed.

In summary, these results demonstrate the feasibility of using the thiolactone bifunctional chelating agent, to generate highly stable and viable Tc-99m labeled proteins products high yield under mild conditions. The combination of the BCA and exchange labeling using [Tc-99m]glucoheptonate yield very stable products and prevents the problem of contaminating colloids, and the labeling of weak binding sites on the protein.

MATERIALS AND METHODS

In carrying out the foregoing experiments, the following materials were used. The following solvents were reagent grade and were used as received: n-hexane, n-pentane, diethyl ether, benzene, acetonitrile, ethyl acetate, methylene chloride, methanol, and absolute ethanol. Dry tetrahydrofuran (THF) was prepared by first drying over anhydrous $CaCl_2$ followed by distillation over Na/benzophenone. HF, HCl and $NH_3$ gases were obtained from Matheson. $N_2$ (pp) gas was obtained from the Baltimore Oxygen Company. Isobutyraldehyde (gold label), sulfur monochloride ($S_2Cl_2$), ethylenediamine, sodium borohydride ($NaBH_4$), 50% KF on celite, lithium aluminum hydride (LAH, 95%), 1,2,2,6,6-pentamethylpiperidine (pempidine), p-methoxybenzyl chloride (stabilized with $CaCO_3$), ethyl-2-bromoacetate, 2-bromoacetic acid, benzylamine and Ellman's reagent, 5,5'-dithio-bis-(2-nitrobenzoic acid), was purchased from the Aldrich Chemical Company. Crystalline human serum albumin (HSA) was purchased from the Sigma Chemical Company. B72.3, a monoclonal antibody against colon carcinoma, and $^{99m}$Tc glucoheptonate kits ("Glucoscan" kits) were gifts from E.I. Dupont de Nemours Co. Inc., N. Billerica, Mass. The polyclonal antiferritin antibody was a gift of Dr. Stanley Order of the Johns Hopkins Medical Institutions. The anti-Rauscher Leukemia monoclonal antibody was a gift of Dr. Mette Strand of the Johns Hopkins University School of Medicine. [$^{125}$I]NaI was purchased from Amersham as an aqueous solution at a pH 9-10. [$^{99m}$Tc]NaTcO$_4$ was obtained as a saline solution from a $^{99}$Mo/$^{99m}$Tc generator purchased from Cintichem and Union Carbide. Silica (1000 and 2000 μ) and alumina (1000 μ) preparative chromatographic plates were obtained from Analtech. Silica and alumina 250 μ analytical TLC plates (Machery-Nagel) were obtained from Brinkmann. Bulk radioiodine gel filtration pre-column material and gel filtration HPLC Columns (Protein Pak 300SW), were purchased from Waters Chromatography Division of Millipore. PD-10 disposable columns were obtained from Pharmacia. Melting points are reported uncorrected using a Thomas Hoover capillary melting point apparatus. The Kugelrohr distillation apparatus was purchased from Aldrich Chemical Company. Infrared spectroscopy was performed on a Perkin-Elmer 399B spectrophotometer. Spectrophotometric determinations were made on a Perkin-Elmer Lambda 5 UV/visible spectrophotometer. NMR spectroscopy was performed on the IBM Instruments Inc. NR/80 FT-NMR spectrometer operated at 80.06MHz for protons ($^1$H) and 20.25MHZ for carbon-13 ($^{13}$C). Radioactivity was measured on either the Capintec radioisotope dose calibrator, CRC-7, or Packard Instruments automatic scintillation counter 5986. Elemental combustion analysis was performed by Atlantic Microlabs, Norcross, Ga.

High Performance Liquid Chromatography (HPLC) was performed on a Perkin-Elmer Series 2 instrument equipped with a Perkin-Elmer LC-75 ultraviolet/visible detector; a 2 inch calcium fluoride flow-through scintillation detection system; EE & G/Ortec single-channel analyzer, amplifiers and ratemeters; and a Hewlett Packard HP 339A integrating recorder. In all cases, the eluent was continuously monitored on-line for protein by absorbance (280 nm) and for radioactivity. Particular HPLC columns, mobile phases and flow rates are given for the individual experiments. Spectrophotometric determinations were made on a Perkin-Elmer Lambda 5 UV/visible spectrophotometer.

Male CD-1 mice (average weight 25 g) were purchased from the Charles River Laboratories. Female New Zealand White rabbits (average weight 20 kg) were purchased from Bunnyville.

What is claimed is:

1. A ligand capable of forming a coordination complex with a metal, said ligand comprising the reaction product of:
  (i) a bifunctional ligand capable of reaction with a protein, protein fragment, peptide, amino acid, natural or synthetic analogs thereof or simple molecules containing amino, thiolate, alcholate or other nucleophilic group capable of reacting with a thiolactone and a metal, said ligand having the structure:

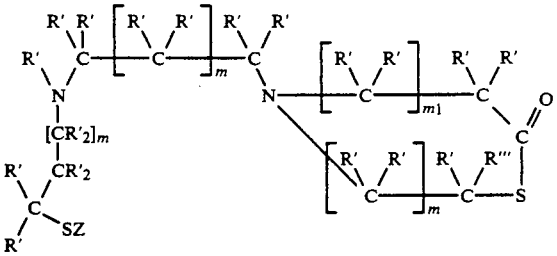

where Z = H, or labile thiol- protecting group

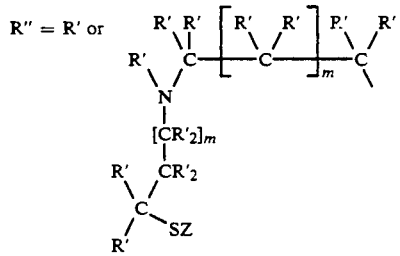

wherein each R' is independently a hydrogen atom or an alkyl group or substituted alkyl group; each R" is independently a hydrogen atom, an alkyl group or the defined group, R'" is independently a hydrogen atom or an alkyl group; m and m$_1$ are 0 or 1, Z is a hydrogen atom or a labile thiol protecting group, and the simple salts thereof, and
  (ii) a compound containing an amino, thiolate, alcolate or any other nucleophilic group capable of reacting with a thiolactone.

2. A ligand as set forth in claim 1 in which the compound containing the amino, thiolate or alcolate group is a protein, protein fragment, peptide, amino acid, natural or synthetic analogs thereof.

3. A ligand as set forth in claim 2 in which the protein of the compound is human serum albumin or fibrinogen.

4. A ligand as set forth in claim 2 in which the protein of the compound is an antibody.

5. A ligand as set forth in claim 4, wherein the antibody is selected from the group consisting of anticolon carcinoma monoclonal antibody, anti-Rausher leukemia monoclonal nntibody or polyclonal anti-ferritin antibody.

6. A ligand as set forth in claim 1 in which the compound containing an amino group is benzylamine or any other amine containing compound.

7. A coordination compound comprising the technetium 1:1 complex of the ligand set forth in claim 1.

8. A coordination compound comprising the technetium 1:1 complex of the ligand set forth in claim 3.

9. A coordination compound comprising the technetium 1:1 complex of the ligand set forth in claim 4.

UNITED STATES PATENT AND TRADEMARK OFFICE
CERTIFICATE OF CORRECTION

PATENT NO. : 5,196,515
DATED : March 23, 1993
INVENTOR(S) : Lever et al.

It is certified that error appears in the above-indentified patent and that said Letters Patent is hereby corrected as shown below:

In Column 1, after line 8 and before line 9, insert --The invention described herein was funded in part by a grant or award from the National Institutes of Health.--.

Signed and Sealed this

Twenty-seventh Day of September, 1994

Attest:

BRUCE LEHMAN

Attesting Officer  Commissioner of Patents and Trademarks